United States Patent [19]

Lippsmeier et al.

[11] 3,997,611
[45] *Dec. 14, 1976

[54] PRODUCTION OF TERTIARY PHOSPHINE OXIDES

[75] Inventors: Bernd Lippsmeier, Hürth-Knapsack; Klaus Hestermann, Erftstadt Bliesheim; Hubert Neumaier, Hürth-Knapsack, all of Germany

[73] Assignee: Hoechst Aktiengesellschaft, Frankfurt am Main, Germany

[*] Notice: The portion of the term of this patent subsequent to Dec. 21, 1993, has been disclaimed.

[22] Filed: Mar. 26, 1975

[21] Appl. No.: 562,222

[30] Foreign Application Priority Data

Apr. 1, 1974 Germany .......................... 2415801

[52] U.S. Cl. .......................................... 260/606.5 P
[51] Int. Cl.² .......................................... C07F 9/02
[58] Field of Search .......................... 260/606.5 P

[56] References Cited

UNITED STATES PATENTS 3,732,316   5/1973   Chingtsung ................. 260/606.5 P

OTHER PUBLICATIONS

Epstein et al., Tetrahedron Letters, V18, pp 1231–1242, pp. 1211–1219, (1962).
Buckler, J.A.C.S. V82, pp. 4215–4220, (1960).
Buckler et al., J.A.C.S. V82, pp. 2076–2077, (1960).
Trippett, J. Chem. Soc. pp. 2813–2816, (1961).
Hellmann et al., Ann. V659, pp. 49–63, (1962).
Petrov et al., Russ. Chem. Revs. V37, pp. 537–539, (1968).
Kosolapoff et al., Organic Phosphorous Compounds, Wiley–Interscience, N.Y.V.1, pp. 99, 100, (1972).
Cotton, Progress in Inorganic Chemistry, Interscience Publ. N.Y., vol. 5, pp. 47–49, (1963).

*Primary Examiner*—Helen M. S. Sneed
*Attorney, Agent, or Firm*—Connolly and Hutz

[57] ABSTRACT

Production of tertiary phosphine oxides of the general formula (I):

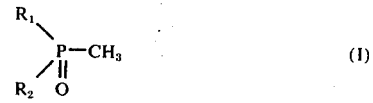

in which the substituents $R_1$ and $R_2$, being identical or different, each stand for an alkyl, alkenyl, alkinyl, cycloalkyl, aralkyl or aryl radical having from 1 to 18 carbon atoms. The phosphine oxides are made by splitting off formaldehyde and hydrogen halide at temperatures within the range about 150° and 350° C, in the presence of hydrogen halide, from a molten compound of the general formula (II):

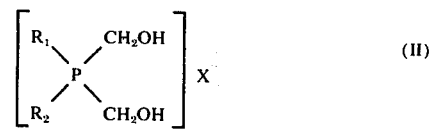

in which $R_1$ and $R_2$ have the meanings given above and X stands for halogen; separating the formaldehyde and hydrogen split off from the reaction mixture, and treating the resulting crude product so as to separate the compound of general formula (I) therefrom.

9 Claims, No Drawings

PRODUCTION OF TERTIARY PHOSPHINE OXIDES

The present invention relates to a process for making tertiary phosphine oxides of the general formula (I):

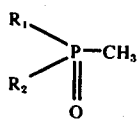

(I)

in which the substituents $R_1$ and $R_2$, being identical or different, each stand for a branched and/or unbranched alkyl, alkenyl or alkinyl radical or, if desired, for a substituted cycloalkyl, aralkyl or aryl radical having from 1 to 18 carbon atoms.

It is known (Houben-Weyl), Methoden der organischen Chemie, Georg Thieme Verlag, Stuttgart, volume XII/1, Page 47 (1963) that quaternary alkyl or arylphosphonium halides can be split into the corresponding tertiary phosphine and alkyl or arylhalide by heating them to temperatures higher than 300° C, with reversal of their mode of formation. In some cases, a mixture comprised of an olefin and hydrogen halide is obtained instead of the alkyl or aryl halide.

It is also known (Houben-Weyl, Methoden der organischen Chemie, Georg Thieme Verlag, Stuttgart, volume XII/1, page 144 (1963) that quaternary phosphonium salts can be treated with moist silver oxide or a strong aqueous alkaline liquor and thereby transformed to the corresponding quaternary phosphonium hydroxides. These are rather unstable compounds. On heating a solution thereof or the residue obtained after evaporation of such solution, they are transformed - an organic radical being split off - into tertiary phosphine oxides in accordance with the following reaction equation (II):

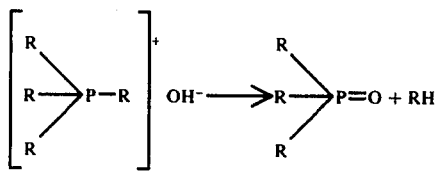

(II)

The process just described enables, for example, methyldiethylphosphine oxide to be produced in the following manner: A solution of methyldiethylphenylphosphonium iodide in water is heated with an excess of silver oxide on a water bath for as long as necessary to have a solution free from iodine ions. The clear solution is filtered, strongly concentrated over a free flame and the residue is distilled. Water and benzene are obtained as the first runnings, while phosphine oxide passes over at 230° C and solidifies on cooling.

The process described heretofore for making tertiary phosphine oxides have a series of adverse effects. In an attempt to obtain yields satisfactory to some extent, it is necessary for the expensive silver oxide to be used in considerable excess quantities and, after the reaction, for the precipitated silver halide and silver oxide in excess to be filtered off, which means considerable expenditure of material and work. A further handicap resides in the fact that the substituents in phosphorus are irregularly fast therewith, so that mixtures of various tertiary phosphine oxides which are difficult to separate from each other by expensive methods, are often obtained.

The present invention now provides a process which avoids the adverse effects referred to hereinabove.

The process of the present invention for making tertiary phosphine oxides of the general formula (I):

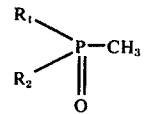

(I)

in which the substituents $R_1$ and $R_2$, being identical or different, each stand for a branched and/or unbranched alkyl, alkenyl or alkinyl radical or, if desired, for a substituted cycloalkyl, aralkyl or aryl radical having from 1 to 18 carbon atoms, comprises: splitting off formaldehyde and hydrogen halide at temperatures within the range about 150° and 350° C in the presence of hydrogen halide from a molten compound of the general formula (II):

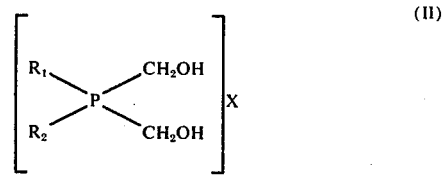

(II)

in which $R_1$ and $R_2$ have the meanings given above and X stands for halogen; separating the formaldehyde and hydrogen halide split off from the reaction mixture, during or after the reaction; and subjecting the resulting crude product to distillation, crystallization or another purifying treatment so as to separate the compound of general formula (I) therefrom.

In accordance with a preferred embodiment of the process of the present invention, the substituents $R_1$ and $R_2$, respectively, stand for a radical having from 1 to 6 carbon atoms or preferably for a methyl, ethyl or cyclohexyl radical, and X stands for chlorine or bromine.

It has also been found advantageous to split off formaldehyde and hydrogen halide from the quaternary phosphonium salt at temperatures within the range 150° and 300° C. The gaseous formaldehyde and hydrogen chloride, respectively, coming from the reactor may be liquefied in a condenser or absorbed in water and re-used for making starting material.

A further preferred embodiment of the process of the present invention comprises: terminating the reaction and then stripping off hydrogen halide, which is dissolved in the molten reaction mixture, by the introduction of nitrogen, carbon dioxide or argon thereinto, or neutralizing the hydrogen halide by means of an alkali metal or alkaline earth metal carbonate and filtering off precipitated alkali metal or alkaline earth metal halide.

The following statements are intended further to illustrate the process of the present invention, which may be effected in the following manner, for example:

The phosphonium salt is placed in a heatable reactor provided with a thermometer, a hydrogen halide inlet opening into the reactor down to its bottom and with an agitator, and heated therein to the reaction temperature within the range about 150° and 350° C, at atmospheric pressure.

As early as during the initial heating period, hydrogen halide should preferably be introduced into the salt so as to have an acid medium in the reaction mixture. Once the reaction has started — this becomes visible by an increased evolution of hydrogen halide and formaldehyde — it is possible to discontinue substantially completely the supply of hydrogen halide. The reaction temperature, which is within the range about 150° and 350° C, is selected in accordance with the melting point and thermal stability of the starting material or the resulting final product. It is preferable for molten starting material to be subjected to reaction at atmospheric pressure.

The reactor is connected to a heatable column and to a condenser downstream thereof, wherein the formaldehyde set free during the reaction is condensed. The hydrogen halide originating from the reaction may be absorbed in water or aqueous sodium hydroxide solution. It is possible for the condenser to be replaced by a scrubbing column charged with water. In this event, the escaping gas is absorbed in water and the resulting aqueous hydrogen halide-containing formalin solution is re-used for making starting material, if desired.

The reaction product may be worked up in known manner by fractional distillation or recrystallization. Hydrogen halide dissolved or absorbed in the reaction product is neutralized by stripping the product with an inert gas, e.g. nitrogen or carbon dioxide, at temperatures above the melting point of the particular phosphine oxide concerned, or by treating the melt with alkali metal or alkaline earth metal carbonates, such as $Na_2CO_3$, $K_2CO_3$ or $CaCO_3$. In this latter case, precipitated alkali metal or alkaline earth metal halide is filtered off and the water originating from the neutralization is removed under vacuum. The resulting phosphine oxide-containing crude product may be purified either by distillation under vacuum, recrystallization or any other known method. A further embodiment comprises working up the entire reaction mixture by fractional distillation under vacuum, without prior filtration. It is also possible for the crude product-salt mixture to be worked up by extracting it with a suitable solvent. In this latter case, the desirable phosphine oxide is obtained after removal of the solvent by distillative treatment.

The process of the present invention avoids the adverse effects encountered heretofore in the splitting of phosphonium salts. More particularly, it avoids the need for filtration of silver halide and the formation of phosphine oxide mixtures which are difficult to separate. Apart from the phosphonium salt used as the starting material, it is only necessary to use a minor amount of gaseous hydrogen halide so as to provide for an acid reaction medium.

In clear contrast with silver halide, it is possible for the formaldehyde and hydrogen halide split off to be used again for making starting material, which is a further beneficial effect of the present process. In other words, the invention provides an ecologically beneficial and commercially very attractive process.

The products of the present invention are valuable intermediates having good interfacial and surface-active properties. In addition thereto, they find use in the dyeing industries, in detergents, for the extractive separation of rare earths and in the catalytic decontamination of off-gases, e.g. for the removal of sulfur compounds from gas mixtures.

EXAMPLE 1

A 500 ml round flask placed in an oil bath and provided with a gas inlet opening thereinto down its bottom, a cooler and a thermometer was supplied with 158.5 g (1 mol) of bis-(hydroxymethyl)-dimethylphosphonium chloride which was heated therein to 225° C within 20 minutes. During the initial heating period, hydrogen chloride was supplied at a rate 3-4 l per hour so as to have an acid reaction mixture from the onset of the reaction. Following this, the whole was heated for a further 2 hours to 225°-230° C, while the quantity of HCl supplied was reduced down to 2-3 l/h. The formaldehyde and hydrogen chloride split off during the reaction were expelled through a column heated to 120° C and condensed. Hydrogen chloride, which was found to escape, was absorbed in water or sodium hydroxide solution. After the reaction was terminated, the reaction mixture was freed from the bulk of hydrogen chloride, which adhered thereto, by introducing nitrogen thereinto over a period of 4 hours at 160° C. The mixture so treated contained 3.2 weight % of HCl. Altogether 28.9 g of formaldehyde, substantially in the form of paraformaldehyde, was obtained.

The reaction product was freed from residual hydrogen chloride in the following manner: A quantity of sodium carbonate equivalent to the quantity of HCl was added at 150°-155° C, the water of neutralization was combined with anhydrous $N_2SO_4$ and precipitated NaCl and hydrated $Na_2SO_4$ were filtered off while hot. Colorless crystalline trimethylphosphine oxide melting at 139°-140° C was obtained in a yield of 68.4 g or 74.3 % of the theoretical. The product was completely free from HCl.

The salt residue filtered off was extracted with methylene chloride and a further 2.3 g of trimethylphosphine oxide was obtained. This corresponded to a total yield of 70.7 g or 76.8 % of the theoretical.

EXAMPLE 2

The apparatus was the same as that used in Example 1 save that it was connected to a heated scrubbing column having water therein. 158.5 g (1 mol) of bis-(hydroxymethyl)-dimethylphosphonium chloride was heated in the manner described in Example 1 to 235°-240° C and kept at that temperature for altogether 3 hours. The formaldehyde and hydrogen chloride split off were expelled through the column heated to 140° C and water-scrubbed in the scrubber placed downstream thereof. An aqueous formalin solution in hydrochloric acid, containing altogether 24.4 g of HCl and 29.4 g of formaldehyde, was obtained.

The reaction product contained 22.9 weight % of HCl. The melt was admixed at 130° C with agitation with an equivalent quantity of $K_2CO_3$ and the water of neutralization was distilled off. Once $CO_2$ ceased to be evolved, the whole was dehydrated with anhydrous $Na_2SO_4$ so as to remove residual water, and the trimethylphosphine oxide obtained was subjected to sublimation under vacuum. A colorless product which crystallized on cooling was obtained in a yield of 73.5 g or 79.9 % of the theoretical. The product had a melting point of 140°-141° C.

EXAMPLE 3

The apparatus was the same as that described in Example 1, in which 80 g (0.27 mol) of bis-(hydroxymethyl)-dicyclohexylphosphonium chloride was rapidly heated to 175° C. The melt was stirred and 2–3 l of hydrogen chloride was introduced thereinto, while the temperature was increased to 210°–215° C. The formaldehyde and hydrogen chloride split off during the reaction were expelled in the manner described in Example 1, through the heated column, and condensed or absorbed. 97 % of the formaldehyde and 99 % of the hydrogen chloride split off were obtained. The reaction period was altogether 2 hours. The melt was stripped with nitrogen to remove minor amounts of dissolved or absorbed hydrogen chloride therefrom. Following this, the slightly yellowish reaction product was distilled under vacuum. A colorless crystalline product melting at 88°–90° C and boiling at 151°–152° C under 0.3 mm Hg was obtained in a yield of 52.5 g or 84.6% of the theoretical.

We claim:

1. A process for making tertiary phosphine oxides of the general formula (I):

in which $R_1$ and $R_2$ are selected from the group consisting of alkyl, alkenyl, alkinyl, cycloalkyl, aralkyl and aryl having from 1 to 18 carbon atoms, which comprises splitting of formaldehyde and hydrogen halide at temperatures within the range about 150° and 350° C, in the presence of hydrogen halide, from a molten compound of the general formula (II):

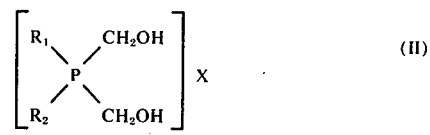

in which $R_1$ and $R_2$ have the meanings given above, and X is halogen; separating the formaldehyde and hydrogen halide split off from the reaction mixture, during or after the reaction; and separating the compound of general formula (I) from the crude product.

2. The process as claimed in claim 1, wherein $R_1$ and $R_2$ each have from 1 to 6 carbon atoms.

3. The process as claimed in claim 2, wherein $R_1$ and $R_2$ are methyl, ethyl or cyclohexyl.

4. The process as claimed in claim 1, wherein X is chlorine or bromine.

5. The process as claimed in claim 1, wherein the formaldehyde and hydrogen halide are split off at a temperature within the range 150 and 300° C.

6. The process as claimed in claim 1, wherein gaseous formaldehyde and hydrogen chloride, respectively, originating from, and escaping during, the reaction are liquefied in a condenser or absorbed in water.

7. The process as claimed in claim 1, wherein, following termination of the reaction, the molten reaction mixture is freed from hydrogen halide dissolved therein by stripping with nitrogen, carbon dioxide or argon.

8. The process as claimed in claim 1, wherein, following termination of the reaction, the hydrogen halide dissolved in the molten reaction mixture is neutralized by means of alkali metal or alkaline earth metal carbonates and precipitated alkali metal or alkaline earth metal halide is filtered off.

9. The process as claimed in claim 1, wherein the crude product is distilled or crystallized so as to separate the compound of general formula (I) therefrom.

* * * * *